US011613717B2

(12) United States Patent
Leal et al.

(10) Patent No.: US 11,613,717 B2
(45) Date of Patent: Mar. 28, 2023

(54) METHOD OF PRODUCING A FUEL ADDITIVE

(71) Applicants: SABIC GLOBAL TECHNOLOGIES B.V., Bergen op Zoom (NL); SAUDI ARABIAN OIL COMPANY, Dhahran (SA)

(72) Inventors: Guillermo Leal, Riyadh (SA); Kareemuddin Mahaboob Shaik, Dhahran (SA); Mohammed Bismillah Ansari, Riyadh (SA); Hiren Shethna, Dhahran (SA); Zhonglin Zhang, Dhahran (SA)

(73) Assignees: SABIC GLOBAL TECHNOLOGIES B.V., Bergen op Zoom (NL); SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 16/633,311

(22) PCT Filed: Jul. 27, 2018

(86) PCT No.: PCT/IB2018/055647
§ 371 (c)(1),
(2) Date: Jan. 23, 2020

(87) PCT Pub. No.: WO2019/021257
PCT Pub. Date: Jan. 31, 2019

(65) Prior Publication Data
US 2020/0157450 A1  May 21, 2020

Related U.S. Application Data

(60) Provisional application No. 62/537,503, filed on Jul. 27, 2017.

(51) Int. Cl.
| | |
|---|---|
| *C07C 6/04* | (2006.01) |
| *C07C 29/04* | (2006.01) |
| *C07C 41/06* | (2006.01) |
| *C10L 10/10* | (2006.01) |
| *C10L 1/182* | (2006.01) |
| *C07C 5/25* | (2006.01) |

(52) U.S. Cl.
CPC ............ *C10L 10/10* (2013.01); *C07C 5/2506* (2013.01); *C07C 6/04* (2013.01); *C07C 29/04* (2013.01); *C07C 41/06* (2013.01); *C10L 1/182* (2013.01)

(58) Field of Classification Search
CPC ........................ C10G 2300/80; C10G 2400/20; C10G 69/02; C10G 45/32; C07C 6/04; C07C 29/04; C07C 41/06; C07C 5/05; C07C 5/13; C07C 5/22
See application file for complete search history.

(56) References Cited

U.S. PATENT DOCUMENTS

| | | |
|---|---|---|
| 3,061,654 A | 10/1962 | Gensheimer et al. |
| 3,797,690 A | 3/1974 | Taylor et al. |
| 3,849,062 A | 11/1974 | Kozlowski et al. |
| 3,912,463 A | 10/1975 | Kozlowski et al. |
| 4,324,936 A | 4/1982 | Mikulicz |
| 4,334,890 A | 6/1982 | Kochar et al. |
| 4,336,046 A | 6/1982 | Schorre et al. |
| 4,356,339 A | 10/1982 | Imaizumi et al. |
| 4,408,085 A | 10/1983 | Gottlieb et al. |
| 4,423,251 A | 12/1983 | Pujado et al. |
| 4,436,946 A * | 3/1984 | Smutny ............. C07C 2/14 585/510 |
| 4,455,445 A | 6/1984 | Neuzil et al. |
| 4,499,313 A | 2/1985 | Okumura et al. |
| 4,540,831 A | 9/1985 | Briggs |
| 4,773,968 A | 9/1988 | O'Connell et al. |
| 4,783,555 A | 11/1988 | Atkins |
| 4,797,133 A | 1/1989 | Pujado |
| 4,927,977 A | 5/1990 | Child et al. |
| 5,227,553 A | 7/1993 | Polanek et al. |
| 5,254,748 A | 10/1993 | Hensley et al. |
| 5,382,707 A * | 1/1995 | Rubin ............. C07C 41/06 568/697 |
| 5,523,502 A * | 6/1996 | Rubin ............. C07C 11/04 568/697 |
| 5,563,299 A | 10/1996 | Paludetto et al. |
| 5,628,880 A | 5/1997 | Hearn et al. |

(Continued)

FOREIGN PATENT DOCUMENTS

| | | | |
|---|---|---|---|
| CA | 2018524 A1 * | 12/1990 | ............. C07C 41/06 |
| CN | 1044804 C | 8/1999 | |

(Continued)

OTHER PUBLICATIONS

Co-pending U.S. Appl. No. 16/981,183, filed Sep. 15, 2020.*
Co-pending U.S. Appl. No. 16/981,189, filed Sep. 15, 2020.*
Co-pending U.S. Appl. No. 17/042,614, filed Sep. 28, 2020.*
Co-pending U.S. Appl. No. 17/045,669, filed Oct. 6, 2020.*
Co-pending U.S. Appl. No. 17/052,407, filed Nov. 2, 2020.*
And co-pending U.S. Appl. No. 17/054,906, filed Nov. 12, 2020.*
Fuel Additives Selection Guide: Types, Features, Applications, Engineering 360, 4 pages, obtained May 11, 2022, https://www.globalspec.com/learnmore/materials_chemicals_adhesives/industrial_oils_fluids/fuel_oil_fluid_additives (Year: 2022).*
International Search Report; International Application No. PCT/IB2018/055647; International Filing Date: Jul. 27, 2018; dated Oct. 30, 2018; 6 pages.

(Continued)

*Primary Examiner* — Rosalynd A Keys
(74) *Attorney, Agent, or Firm* — Cantor Colburn LLP

(57) ABSTRACT

A method of producing a fuel additive includes passing a feed stream comprising C4 hydrocarbons through a methyl tertiary butyl ether unit producing a first process stream; passing the first process stream through a selective hydrogenation unit producing a second process stream; passing the second process stream through an isomerization unit producing a third process stream; and passing the third process stream through a hydration unit producing the fuel additive and a recycle stream.

20 Claims, 1 Drawing Sheet

(56) References Cited

U.S. PATENT DOCUMENTS

| | | | |
|---|---|---|---|
| 5,672,795 A * | 9/1997 | Vora | C07C 41/06 |
| | | | 568/697 |
| 5,877,365 A | 3/1999 | Chodorge et al. | |
| 5,898,091 A * | 4/1999 | Chodorge | C10G 69/02 |
| | | | 585/647 |
| 5,955,640 A | 9/1999 | Paludetto et al. | |
| 7,227,047 B2 | 6/2007 | Risch et al. | |
| 7,459,593 B1 * | 12/2008 | Krupa | C07C 6/04 |
| | | | 585/329 |
| 7,473,812 B2 | 1/2009 | Peters et al. | |
| 7,485,761 B2 | 2/2009 | Schindler et al. | |
| 8,124,572 B2 | 2/2012 | Miller | |
| 8,395,007 B2 | 3/2013 | Wright et al. | |
| 8,999,013 B2 | 4/2015 | Xu et al. | |
| 9,187,388 B2 * | 11/2015 | Arjah | B01J 19/185 |
| 9,611,192 B2 | 4/2017 | Digiulio | |
| 10,774,020 B2 | 9/2020 | Di Girolamo et al. | |
| 2002/0169346 A1 | 11/2002 | Commereuc et al. | |
| 2003/0158429 A1 | 8/2003 | Albiez et al. | |
| 2004/0171891 A1 | 9/2004 | Scholz et al. | |
| 2005/0107628 A1 * | 5/2005 | Roper | C07C 45/50 |
| | | | 558/20 |
| 2005/0288534 A1 | 12/2005 | Fernandez et al. | |
| 2007/0149839 A1 | 6/2007 | Rix et al. | |
| 2007/0265483 A1 | 11/2007 | Himelfarb | |
| 2008/0146858 A1 * | 6/2008 | Elomari | C10G 29/205 |
| | | | 585/331 |
| 2008/0312481 A1 * | 12/2008 | Leyshon | C07C 6/04 |
| | | | 585/324 |
| 2009/0193710 A1 | 8/2009 | Xiong et al. | |
| 2011/0040133 A1 | 2/2011 | Vermeiren et al. | |
| 2011/0230632 A1 | 9/2011 | Abhari | |
| 2012/0117862 A1 * | 5/2012 | Xu | C07C 29/04 |
| | | | 44/452 |
| 2012/0283492 A1 | 11/2012 | Dalemat et al. | |
| 2013/0072732 A1 * | 3/2013 | Breuil | B01J 31/143 |
| | | | 585/251 |
| 2013/0104449 A1 | 5/2013 | Xu et al. | |
| 2013/0172627 A1 | 7/2013 | Chewter et al. | |
| 2013/0331620 A1 | 12/2013 | Abhari | |
| 2014/0039226 A1 | 2/2014 | Xu et al. | |
| 2014/0142350 A1 | 5/2014 | Weiner et al. | |
| 2015/0225320 A1 | 8/2015 | Shaik et al. | |
| 2015/0322181 A1 | 11/2015 | Kim et al. | |
| 2016/0326079 A1 | 11/2016 | Lee et al. | |
| 2017/0073289 A1 | 3/2017 | Leal et al. | |
| 2017/0198231 A1 | 7/2017 | Xu et al. | |

FOREIGN PATENT DOCUMENTS

| | | | | |
|---|---|---|---|---|
| CN | 1506344 A | 6/2004 | | |
| CN | 1736589 A | 2/2006 | | |
| CN | 101279879 A | 10/2008 | | |
| CN | 102070391 A | 5/2011 | | |
| CN | 102372573 A | 3/2012 | | |
| CN | 105585411 A | 5/2016 | | |
| CN | 106608791 A | 5/2017 | | |
| EP | 0063813 B1 | 11/1982 | | |
| EP | 0102840 B1 | 3/1984 | | |
| EP | 0253679 | 1/1988 | | |
| EP | 0605822 A1 | 7/1994 | | |
| GB | 1374368 | 11/1974 | | |
| JP | S5920232 A | 2/1984 | | |
| JP | 2010111596 A | 5/2010 | | |
| PL | 206183 B1 * | 7/2010 | | C07C 7/14891 |
| RU | 2470905 C1 | 12/2012 | | |
| WO | 9011268 | 10/1990 | | |
| WO | 9732838 A1 | 9/1997 | | |
| WO | 0043336 A1 | 7/2000 | | |
| WO | 0146095 A1 | 6/2001 | | |
| WO | 2006113191 A2 | 10/2006 | | |
| WO | 2007024733 A2 | 3/2007 | | |
| WO | 2012095744 A2 | 7/2012 | | |
| WO | WO-2014153570 A2 * | 9/2014 | | B01J 19/0093 |
| WO | 2014160825 A1 | 10/2014 | | |
| WO | 2015089005 A1 | 6/2015 | | |
| WO | 2015123026 A1 | 8/2015 | | |
| WO | 2019207477 A1 | 10/2019 | | |

OTHER PUBLICATIONS

Written Opinion; International Application No. PCT/IB2018/055647; International Filing Date: Jul. 27, 2018; dated Oct. 30, 2018; 11 pages.

Bender et al.; "Selective Hydrogenation in Steam Cracking"; 21st Annual Saudi-Japan Symposium; Catalysts in Petroleum Refining & Petrochemicals; King Fahd University of Petroleum & Minerals; 2011; Abstract only; pp. 1-3.

Brockwell et al.; "Synthesize ethers"; Hydrocarbon Processing, vol. 70, No. 9; 1991; pp. 133-141.

International Search Report for International Application No. PCT/IB2019/052177; International Filing Date Mar. 18, 2019; dated Jun. 26, 2019; 3 pages.

International Search Report for International Application No. PCT/IB2019/052178; International Filing Date Mar. 18, 2019; dated Jun. 26, 2019: 6 pages.

International Search Report for International Application No. PCT/IB2019/053697; International Filing Date May 6, 2019; dated Aug. 28, 2019; 11 pages.

International Search Report for International Application No. PCT/IB2019/057784; International Filing Date Sep. 16, 2019; dated Jan. 7, 2020; 5 pages.

International Search Report for International Application No. PCT/US2019/026985; International Filing Date Apr. 11, 2019; dated May 27, 2019; 6 pages.

International Search Report for International Application No. PCT/US2019/028092; International Filing Date Apr. 18, 2019; dated Jun. 26, 2019; 6 pages.

International Search Report for International Application No. PCT/US2019/028099; International Filing Date Apr. 18, 2019; dated Jun. 26, 2019; 6 pages.

Izquierdo et al.; "Equilibrium Constants for Methyl tert-Butyl Ether Liquid-Phas Synthesis"; J. Chem. Eng. Data, vol. 37; 1992; pp. 339-343.

Kalamaras et al.; "SuperButol—A novel high-octane gasoline blending component"; Fuel, vol. 195; 2017; pp. 165-173.

Streich et al.; "Secure the Best Benefits from C4 Hydrocarbon Processing—Part 1: Separation Sequences"; Hydrocarbon Processing: Process Engineering and Optimization; 2016; 6 pages.

Written Opinion for International Application No. PCT/IB2019/052177; International Filing Date Mar. 18, 2019; dated Jun. 26, 2019; 9 pages.

Written Opinion for International Application No. PCT/IB2019/052178; International Filing Date Mar. 18, 2019; dated Jun. 26, 2019; 9 pages.

Written Opinion for International Application No. PCT/IB2019/053697; International Filing Date May 6, 2019; dated Aug. 28, 2019; 9 pages.

Written Opinion for International Application No. PCT/IB2019/057784; International Filing Date Sep. 16, 2019; dated Jan. 7, 2020; 7 pages.

Written Opinion for International Application No. PCT/US2019/026985; International Filing Date Apr. 11, 2019; dated May 27, 2019; 7 pages.

Written Opinion for International Application No. PCT/US2019/028092; International Filing Date Apr. 18, 2019; dated Jun. 26, 2019; 9 pages.

Written Opinion for International Application No. PCT/US2019/028099; International Filing Date Apr. 18, 2019; dated Jun. 26, 2019; 13 pages.

International Search Report for International Application No. PCT/IB2019/059984; International Filing Date Nov. 20, 2019; dated Feb. 21, 2020; 5 pages.

Written Opinion for International Application No. PCT/IB2019/059984; International Filing Date Nov. 20, 2019; dated Feb. 21, 2020; 8 pages.

(56) References Cited

OTHER PUBLICATIONS

International Search Report for International Application No. PCT/IB2020/051908; International Filing Date Mar. 5, 2020; dated May 29, 2020; 6 pages.
Leal et al. U.S. Appl. No. 17/436,753, entitled "Method of Producing a Fuel Additive", filed Sep. 7, 2021.
Written Opinion for International Application No. PCT/IB2020/051908; International Filing Date Mar. 5, 2020; dated May 29, 2020; 9 pages.
Ansari et al.; U.S. Appl. No. 17/054,906; entitled "Method of Producing a Fuel Additive With a Hydration Unit"; filed Nov. 12, 2020.
Bodas et al.; U.S. Appl. No. 17/292,261; entitled "Process and System for Producing Ethylene and at Least One of Butanol and an Alkyl Tert-Butyl Ether"; filed May 7, 2021.
Leal et al.; U.S. Appl. No. 17/264,430; entitled "Systems and Processes for Efficient Production of One or More Fuel Additives"; filed Jan. 29, 2021.

\* cited by examiner

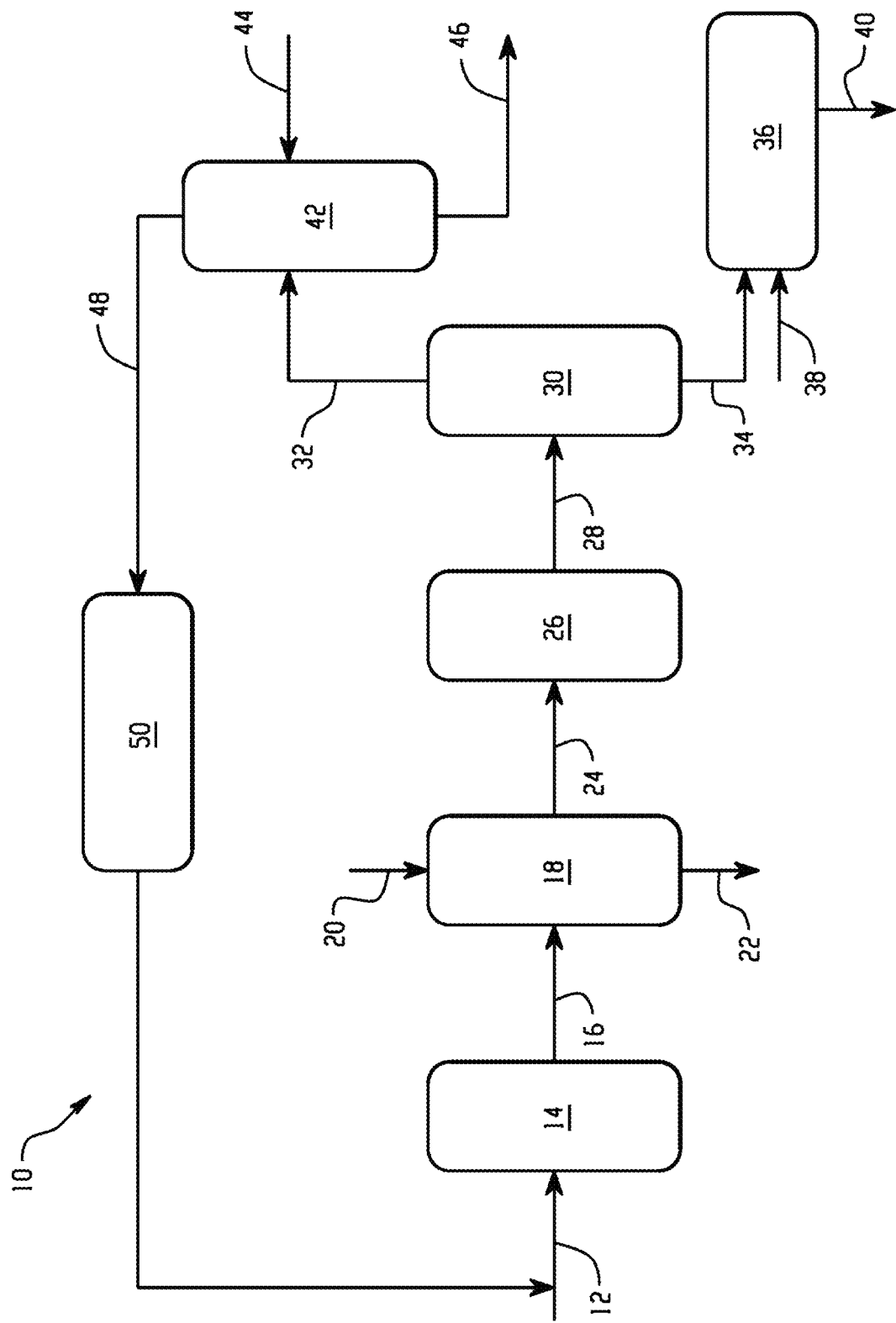

METHOD OF PRODUCING A FUEL ADDITIVE

CROSS REFERENCE TO RELATED APPLICATIONS

This application is a National Stage application of PCT/IB2018/055647 filed Jul. 27, 2018, which is incorporated herein by reference in its entirety, and which claims the benefit of U.S. Application No. 62/537,503, filed Jul. 27, 2017.

BACKGROUND

Commercial gasoline, which is fuel for internal combustion engines, is a refined petroleum product that is typically a mixture of hydrocarbons (base gasoline), additives, and blending agents. Additives and blending agents are added to the base gasoline to enhance the performance and the stability of gasoline, for example, such additives can include octane boosters.

When used in high compression internal combustion engines, gasoline has the tendency to "knock." Knocking occurs when combustion of the air/fuel mixture in the cylinder does not start off correctly in response to ignition because one or more pockets of air/fuel mixture pre-ignite outside the envelope of the normal combustion front. Anti-knocking agents, also known as octane boosters, reduce the engine knocking phenomenon, and increase the octane rating of the gasoline.

Hydrocarbon cracking processes are important conversion processes used in petroleum refineries. For example, fluid catalytic cracking (FCC) is widely used to convert the high-boiling, high-molecular weight hydrocarbon fractions of petroleum crude oils to more valuable gasoline, olefinic gases, and other products. Thermal cracking of naphtha and gas oil is also widely used in the petrochemical industry to produce a variety of olefins and aromatics. For example, hydrocarbon feed stocks can be mixed with steam and subjected to elevated temperatures (e.g., 700-900° C.) in a steam cracker furnace wherein the feed stock components are cracked into various fractions. The effluent of the steam cracker can contain a gaseous mixture of hydrocarbons, for example, saturated and unsaturated olefins and aromatics (C1-C35). The effluent can then be separated into individual olefins (for example, ethylene, propylene and C4's) and pyrolysis gasoline. Recycle streams of crude hydrocarbons are often formed as byproducts during these cracking processes.

The presence of isobutylene, butadiene, 1-butene, 2-butene, and other components within the crude hydrocarbon streams can allow for the formation of valuable alcohols and fuel additives. Such alcohols can include methanol, which is commonly used as a gasoline octane booster. However, the conversion of crude hydrocarbon streams to fuel additive products can often be inefficient and costly. Furthermore, the final product specifications for such alcohols can be undesirable and can fail to meet market quality requirements. For example, alcohol products can have high levels of impurities, high Reid vapor pressures, e.g., greater than 2.0 pounds per square inch (psi) (greater than 10 kilopascals), and low octane numbers (e.g., 82 Research Octane Number (RON)), all of which correlate with poor product quality. Any improvement in these specifications and/or the efficiency of the process can provide a more valuable fuel additive product.

Thus, there is a need for an efficient method of producing fuel additives that can make use of crude hydrocarbon streams and produce final products with low impurities and high performance specifications.

SUMMARY

Disclosed, in various embodiments, are methods of producing fuel additives.

A method of producing a fuel additive includes: passing a feed stream comprising C4 hydrocarbons through a methyl tertiary butyl ether unit producing a first process stream; passing the first process stream through a selective hydrogenation unit producing a second process stream; passing the second process stream through an isomerization unit producing a third process stream; and passing the third process stream through a hydration unit producing the fuel additive and a recycle stream.

A method of producing a fuel additive includes: passing a first feed stream comprising C4 hydrocarbons through a catalytic cracking unit producing a second feed stream, wherein the first feed stream comprises ethyl acetylene, vinyl acetylene, 1,3-butadiene, 1,2-butadiene, isobutylene, cis-2-butene, trans-2-butene, 1-butene, isobutane, n-butane, or a combination comprising at least one of the foregoing; passing the second feed stream through a methyl tertiary butyl ether unit producing a first process stream and a methyl tertiary butyl ether product and withdrawing the methyl tertiary butyl ether product from the methyl tertiary butyl ether unit, wherein less than 99.99% of any isobutylene present in the feed stream is converted to methyl tertiary butyl ether within the methyl tertiary butyl ether unit; passing the first process stream through a hydrogenation unit producing a second process stream, wherein greater than or equal to 90% of any butadiene present in the first process stream is converted to 2-butene, 1-butene and n-butane within the hydrogenation unit; passing the second process stream through an isomerization unit producing a third process stream, wherein less than or equal to 99.99% of any 1-butene present in the second process stream is converted to 2-butene within the isomerization unit; passing the third process stream through a hydration unit, wherein the third process stream comprises less than or equal to 0.1% butadiene by weight prior to passing through the hydration unit; withdrawing a fuel additive product from the hydration unit, wherein the fuel additive product comprises greater than 0.1% trimethylpentane; withdrawing a raffinate stream from the hydration unit and recycling the raffinate stream to the catalytic cracking unit; and passing a bottom stream of the isomerization unit through a metathesis unit and withdrawing a propylene product from the metathesis unit.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

FIG. 1 is a schematic diagram representing a unit sequence for producing fuel additives.

DETAILED DESCRIPTION

Disclosed herein is an efficient method of producing fuel additives that can make use of crude hydrocarbon streams and produce final products with low impurities and high performance specifications. For example, the method disclosed herein can provide a unique sequence of unit operations that converts crude hydrocarbons into valuable fuel additives, such as alcohol fuel additives. This unique sequence can significantly improve the efficiency of the process, thereby reducing total capital costs. The final fuel additive products can have levels of trimethylpentane of 0.01 weight % to 50 weight %, based on the total weight of the fuel additive, high octane numbers (e.g., greater than or equal to 85 RON, or greater than or equal to 87 RON), and low Reid vapor pressures of greater than or equal to 55 Kilopascals. For example, the trimethylpentane can be present in an amount of 0.1 to 25 weight percent, for example, 1 to 20 weight %. Any one or all of these properties can correlate with high performance and high market value. The method disclosed herein can also produce secondary products along with the fuel additive product. For example, both propylene and methyl tertiary butyl ether (MTBE) products can be produced along with the fuel additive, thus maximizing the efficiency and productivity of the process.

The method disclosed herein can utilize 2-butene with traces of 1-butene e.g., in amounts of less than or equal to 0.01 weight percent to maximize the amount of trimethylpentane (e.g., 2-butanol and tertbutyl alcohol (TBA)) in the final fuel additive product, which can be used to produce propylene. To achieve a maximum increase in the production of 2-butene from a butadiene component present in the C4 hydrocarbon feed stream, isomerization can occur by passing the feed stream through an isomerization unit leaving traces of butadiene that can be less than or equal to 1.0% by weight, for example, less than or equal to 0.5% by weight, for example, less than or equal to 0.1% by weight. A MBTE synthesis unit can be inserted in the process to convert isobutylene through a reaction with a methanol stream to produce MTBE. The method can produce a fuel additive containing a maximum volume of alcohols, for example, mixed alcohols, for example, C4 alcohols, with a minimum amount of butadiene, e.g., less than or equal to 0.1% by weight in the feed stream.

The method disclosed herein can include passing a stream of crude hydrocarbons through a MTBE unit producing a first process stream. The MTBE unit can convert isobutylene present in the feed stream to a MTBE product. The first process stream can then be passed through a selective hydrogenation unit. This selective hydrogenation unit can convert the butadiene present in the first process stream to 2-butene and produce a second process stream. The second process feed stream can then be passed through an isomerization unit, for example, a hydroisomerization unit, which can convert the 1-butene present in the second process stream to 2-butene. A third process stream taken from the isomerization unit can then be passed through a hydration unit to produce a fuel additive, for example, an alcohol fuel additive, such as a mixed alcohol fuel additive, such as a C4 alcohol fuel additive. The maximization of 2-butene in the process increases desirable product specifications, such as octane number. Optionally, a bottom stream of the isomerization unit can be passed through a metathesis unit in order to produce propylene as a secondary product. The present process can maximize product quality for a fuel additive product while also producing additional secondary products in an efficient manner.

The method disclosed herein can include passing a feed stream through an olefin production unit, for example, a hydrocarbon cracking unit, for example, a catalytic and/or steam cracking unit, such that a source of the feed stream can include a product of an olefin cracking process and/or an olefin production process. The feed stream can comprise hydrocarbons, for example, C4 hydrocarbons. Additional hydrocarbons, for example, C2 and C3 hydrocarbons, can also be fed to the olefin production unit. The feed stream can then be withdrawn from the olefin production unit as a crude C4 hydrocarbon stream. The process stream produced by the olefin production unit can comprise ethyl acetylene, vinyl acetylene, 1,3-butadiene, 1,2-butadiene, isobutylene, cis-2-butene, trans-2-butene, 1-butene, isobutane, n-butane, or a combination comprising at least one of the foregoing.

The feed stream can then be passed through a MTBE unit producing a first process stream. Methanol can be fed through the MTBE unit via a methanol stream. The MTBE unit can convert isobutylene present in the process stream to a MTBE product. This MTBE product can be withdrawn from the MTBE unit via an MTBE product stream. The purity of the MTBE product can be greater than or equal to 90%. The conversion rate from isobutylene to MTBE within the MTBE unit can be greater than or equal to 75%, for example, greater than or equal to 85%, for example, greater than or equal to 90%. The first process stream can then be withdrawn from the MTBE unit with reduced isobutylene content. For example, the first process stream exiting the MTBE unit can comprise less than or equal to 2.0% by weight isobutylene. A temperature within the MTBE unit can be 100° C. to 225° C. A pressure within the MTBE unit can be 50 kiloPascals to 1200 kiloPascals, for example, 50 kiloPascals to 500 kiloPascals, for example, 100 kiloPascals to 350 kiloPascals, for example, 150 kiloPascals to 250 kiloPascals, for example, 198 kiloPascals to 230 kiloPascals. The reaction can be carried out in a fixed bed reactor where the temperature can be maintained at a temperature of 30 to 100° C. and the pressure can be maintained at a pressure of 710 to 1200 kiloPascals.

The first process stream exiting the MTBE unit can then be passed through a selective hydrogenation unit. For example, the selective hydrogenation unit can be a selective butadiene hydrogenation unit. The process stream entering the hydrogenation unit can comprise less than or equal to 75% by weight butadiene, for example, less than or equal to 50% by weight, for example, less than or equal to 40% by weight. The hydrogenation unit can convert butadiene present in the process stream to 2-butene. The yield from butadiene to 2-butene can be greater than or equal to 30% and from butadiene to butene 1 greater that 65%. It is to be noted, however that the selectivities can be shifted to either butene-1 or butene-2 depending on the requirements of the various downstream units. The selective hydrogenation unit can comprise multiple reactors in series, for example, the unit can comprise three reactor stages. The first two reactor stages can convert butadiene present in the first process stream to 2-butene. The first two reactors can comprise a selective hydrogenation catalyst. For example, the hydrogenation catalyst can comprise palladium with an aluminum base. The hydrogenation catalyst can comprise platinum, rhodium, palladium, ruthenium, cobalt, nickel, copper, or a combination comprising at least one of the foregoing. The catalyst can be the same for the first two reactors. Hydrogen can be injected into the first process stream prior to passing through the first reactor stage.

Final hydrogenation reaction of di-olefins to a desired product of mono-olefin can be achieved in the third reactor. Carbon monoxide can be injected into the third reactor to attenuate the catalyst and minimize the isomerization reaction from butene-1 to butene-2. During normal operations, the desired carbon monoxide injection rate can be 2 parts per million of the feed stream to the third reactor. The rate can be increased if too much butene-1 is being lost to butene-2. The first process stream can then be withdrawn from the selective hydrogenation unit. Operation conditions for the selective hydrogenation unit are shown in Table 1. Temperature is reported in degrees Celsius and pressure in pounds per square inch gage and kiloPascals.

TABLE 1

| Reactor | Temp ° C. | Pressure (psig) | Catalyst | BD content at exit |
|---|---|---|---|---|
| 1st Reactor | 40-70 | 140-400 (965-2758 kPa) | Noble metal/ Alumina | 7% |
| 2nd Reactor | 50-60 | 140-400 (965-2758 kPa) | Noble metal/ Alumina | 1% |
| 3rd Reactor | 60-80 | 250-270 (1724-1862 kPa) | Noble metal/ Alumina | <0.01% |

The second process stream exiting the hydrogenation unit can then be passed through an isomerization unit, for example, a hydroisomerization unit to produce a third process stream. This isomerization unit can convert the 1-butene present in the third process stream to 2-butene. For example, greater than or equal to 90% of any 1-butene present in the second process stream can be converted to 2-butene within the isomerization unit. Typical reactor inlet temperatures can be 25 to 125° C., for example, 45 to 85° C. F. Typical reactor pressures are 2 to 12 barg (200 to 1200 kPa), for example, 3 to 8 barg (300 to 800 kPa). The third process stream can then be withdrawn from the isomerization unit with maximized 2-butene content. For example, the third process stream exiting the isomerization unit can comprise greater than or equal to 50% by weight 2-butene.

The third process stream exiting the isomerization unit can then be passed through a hydration unit to produce a recycle stream and a fuel additive, for example, an alcohol fuel additive, such as a mixed alcohol fuel additive, such as a C4 alcohol fuel additive. The third process stream entering the hydration unit can comprise less than or equal to 50% butadiene by weight, for example, less than or equal to 45% by weight, for example, less than or equal to 40% by weight. The fuel additive product can be withdrawn from the hydration unit via a product stream. Water can be fed to the hydration unit via a water stream. Operating conditions of the hydration unit can include a temperature of 120 to 200° C. and a pressure of 50 to 100 barg (5000 to 10,000 kPa) with a liquid hourly space velocity (LHSV) of 1 to 1.5 v/v/hr and a water to butenes molar ratio of 5 to 10:1. The hydration unit can comprise an oscillating baffle reactor, a fixed bed reactor, a membrane integrated reactor, or a combination comprising at least one of the foregoing. The hydration unit can convert butene present in the third process stream to butanol. For example, greater than or equal to 75% of the butene present in the third process stream can be converted to butanol within the hydration unit.

The fuel additive product can comprise 2-butanol, tert-butyl alcohol, di-isobutene, dimers of 1-butene, dimers of 2-butene, dimers of isobutene, or a combination comprising at least one of the foregoing. The fuel additive product can comprise greater than or equal to 0.1% by weight trimethylpentane, for example, greater than or equal to 0.5% by weight, for example, greater than or equal to 0.1% by weight. An octane number of the fuel additive product can be greater than or equal to 80, for example, greater than or equal to 82, for example, greater than or equal to 85, for example, greater than or equal to 87, for example, greater than or equal to 90 according to the Anti-Knock Index, for example, greater than or equal to 90.

The octane number is a standard measurement used to gage the performance of an engine or fuel. The higher the octane number, the more compression the fuel is able to withstand before igniting. Fuels with higher octane ratings are generally used in high performance gasoline engines that need higher compression ratios. Fuels with lower octane numbers can be desirable for diesel engines because diesel engines do not compress the fuel, but rather compress only air and then inject fuel into the air which is heated by compression. Gasoline engines rely on ignition of air and fuel compressed together as a mixture, which is ignited at the end of the compression stroke using spark plugs. As a result, high compressibility of fuel is a consideration for gasoline engines.

The Anti-Knock Index is measured by adding the research octane number and the motor octane number and dividing by two, i.e., (RON+MON)/2. The Research Octane Number is determined by running the fuel in a test engine at a speed of 600 revolutions per minute with a variable compression ratio under controlled conditions, and comparing the results with those for mixtures of iso-octane and n-heptane. Motor Octane Number is determined by testing a similar test engine to that used in determining the Research Octane Number but at a speed of 900 revolutions per minute with a preheated fuel mixture, higher engine speed, and variable ignition timing. Depending on the composition, the Motor Octane Number can be about 8 to 12 octanes lower than the Research Octane Number. The research octane number can be greater than or equal to 88, for example, greater than or equal to 91, for example, greater than or equal to 95. The motor octane number can be greater than or equal to 82, for example, greater than or equal to 85, for example, greater than or equal to 90, for example, greater than or equal to 95. Higher octane ratings can give higher amounts of energy needed to initiate combustion. Fuels with higher octane ratings are less prone to auto-ignition and can withstand a greater rise in temperature during the compression stroke of an internal combustion engine without auto-igniting.

Reid vapor pressure is used to measure the volatility of gasoline defined as the absolute vapor pressure exerted by a liquid at 37.8° C. as determined by ASTM D-323. This measures the vapor pressure of gasoline volatile crude oil, and other volatile petroleum products, except for liquefied petroleum gases. Reid vapor pressure is measured in kiloPascals and represents a relative pressure to atmospheric pressure since ASTM D-323 measures the gage pressure of the sample in a non-evacuated chamber. High levels of vaporization are desired for winter starting and operation and lower levels are desirable in avoiding vapor lock during summer heat. Fuel cannot be pumped when vapor is present in the fuel line and winter starting will be difficult when liquid gasoline in the combustion chambers has not vaporized. This means that the Reid vapor pressure is changed accordingly by oil producers seasonally to maintain gasoline engine reliability.

The Reid vapor pressure of the fuel additive product can be less than or equal to 65 kiloPascals, for example, less than or equal to 60 kiloPascals, for example, less than or equal to 55 kiloPascals. The Reid vapor pressure can vary during winter and summer conditions such that the pressure can be at the higher end of the values during the winter and at the lower end of the values during the summer. The fuel additive product can also comprise less than or equal to 1% by weight impurities such as diene. For example, the fuel additive product can comprise less than or equal to 0.1% by weight of butylene dimers.

A recycle stream, e.g., a hydrocarbon recycle stream, can be withdrawn from the hydration unit and recycled to the initial feed stream and/or the olefin production unit, such as a steam cracker unit. The recycle stream can comprise isobutane, n-butane, isobutylene, or a combination comprising at least one of the foregoing. The recycle stream can be optionally passed through a hydrogenation unit prior to returning to the feed stream.

An additional stream (with the same composition as the third process stream entering the hydration unit) can be withdrawn from the isomerization unit and passed through a metathesis unit to produce propylene as a secondary product. The metathesis reactor has a design gauge pressure of 1.0 barg (100 kPa) and a design temperature of 340° C. The de-ethylenizer condenser has a shell design gauge pressure of 24.4 barg (2440 kPa) and a tube design of 16.0 barg (1600 kPa). The shell ad tube design temperature is −55° C.

The de-propylenizer condenser has a shell design gauge pressure of 16.7. barg (1670 kPa) and a tube design of 10.8 barg (1008 kPa). The shell design temperature and the tube design temperature is 125° C. The de-ethylenizer and de-propylenizer reboilers have a shell design gauge pressure of 24.4 bar (2440 kPa) and 17.7 (1770 kPa) bar, respectively. The tube design gage pressure for the same equipment and units is 16.0 barg (1600 kPa) and 11.5 barg (1150 kPa), respectively. The de-ethylenizer and de-propylenizer reboilers have a tube design temperature of 194° C. The de-ethylenizer and de-propylenizer reboilers have a shell design temperature of 125° C. and 143° C. respectively. The de-ethylenizer column and the de-propylenizer columns have a design gauge pressure of 24.4 barg (2440 kPa) and 17.7 barg (1770 kPa), respectively. The de-ethylenizer column and the de-propylenizer column have a design temperature of 125° C. and 140° C. respectively.

The metathesis unit can have the same operating conditions as the hydration unit. The metathesis unit can convert normal butylene and ethylene to polymer grade propylene via metathesis. The two equilibrium reactions that can take place are metathesis and isomerization. Propylene is formed by the metathesis of ethylene and 2-butene, and 1-butene is isomerized to 2-butene as 2-butene is consumed in the metathesis reaction. Ethylene can be fed to the metathesis unit via an ethylene stream. The propylene product can be withdrawn from the metathesis unit via a propylene product stream. The propylene product can have a purity of greater than or equal to 98%, for example, greater than or equal to 98.8%.

A more complete understanding of the components, processes, and apparatuses disclosed herein can be obtained by reference to the accompanying drawings. The FIGURE (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring now to FIG. 1, this simplified schematic diagram represents a unit sequence 10 used in a method for producing fuel additives. The sequence 10 can include passing a first feed stream 12 comprising hydrocarbons through a hydrocarbon cracking unit 14. For example, the hydrocarbon cracking unit 14 can be a steam cracking and/or a catalytic cracking unit.

A second feed stream 16 can then be withdrawn from the cracking unit 14. The second feed stream 16 can comprise crude hydrocarbons, for example, C4 hydrocarbons. The C4 hydrocarbons can be present in an amount of 0.01 to 25 weight %, for example, 1 to 20 weight %. The second feed stream 16 can then be passed through an MTBE unit 18. Methanol can be fed through the MTBE unit 18 via stream 20. The MTBE unit 18 can convert isobutylene present in the second feed stream 16 to an MTBE product 22. This MTBE product 22 can be withdrawn from the MTBE unit 18.

A first process stream 24 can then be withdrawn from the MTBE unit 18, now comprising a reduced isobutylene content. The first process stream 24 can then be passed through a selective hydrogenation unit 26. The selective hydrogenation unit 26 can optionally be a selective butadiene hydrogenation unit and can comprise multiple reactors in series. This selective hydrogenation unit 26 can convert butadiene present in the first process stream 24 to 2-butene.

A second process stream 28 can then be withdrawn from the hydrogenation unit 26 and passed through an isomerization unit 30, for example, a hydroisomerization unit. This isomerization unit 30 can convert the 1-butene present in the second process stream 28 to 2-butene.

A third process stream 32 can then be withdrawn from the isomerization unit 30 and passed through a hydration unit 42 to produce a fuel additive 46, for example, an alcohol fuel additive, for example, a mixed alcohols fuel additive, for example, a C4 fuel additive. The fuel additive 46 can be withdrawn from the hydration unit 42. Water can be fed to the hydration unit via stream 44.

A recycle stream 48, for example, a hydrocarbon recycle stream, can be withdrawn from the hydration unit 42 and recycled to the feed stream 12 and/or the cracking unit 14. Optionally, the recycle stream 48 can be passed through another hydrogenation unit 50 prior to returning to the feed stream 12.

A bottom stream 34 can be withdrawn from the isomerization unit 30 and passed through a metathesis unit 36 to produce propylene as a secondary product. Ethylene can be fed to the metathesis unit 36 via stream 38. The propylene product can be withdrawn from the metathesis unit 36 via product stream 40.

The following examples are merely illustrative of the method of treating pyrolysis gasoline disclosed herein and are not intended to limit the scope hereof. Unless otherwise stated, the examples were based upon simulations.

The methods disclosed herein include(s) at least the following embodiments:

Embodiment 1

A method of producing a fuel additive, comprising: passing a feed stream comprising C4 hydrocarbons through a methyl tertiary butyl ether unit producing a first process stream; passing the first process stream through a selective hydrogenation unit producing a second process stream; passing the second process stream through an isomerization unit producing a third process stream; and passing the third process stream through a hydration unit producing the fuel additive and a recycle stream.

Embodiment 2

The method of Embodiment 1, wherein a source of the feed stream comprises a product of a catalytic cracking process and/or an olefin production process.

Embodiment 3

The method of any of the preceding embodiments, wherein the feed stream comprises ethyl acetylene, vinyl acetylene, 1,3-butadiene, 1,2-butadiene, isobutylene, cis-2-butene, trans-2-butene, 1-butene, isobutane, n-butane, or a combination comprising at least one of the foregoing.

Embodiment 4

The method of any of the preceding embodiments, wherein less than or equal to 99.99% of any isobutylene present in the feed stream is converted to methyl tertiary butyl ether within the methyl tertiary butyl ether unit.

Embodiment 5

The method of Embodiment 4, further comprising withdrawing a methyl tertiary butyl ether product from the methyl tertiary butyl ether unit.

Embodiment 6

The method of any of the preceding embodiments, wherein greater than or equal to 90% of any butadiene present in the first process stream is converted to 1-butene, 2-butene, n-butane, or a combination comprising at least one of the foregoing within the selective hydrogenation unit.

Embodiment 7

The method of any of the preceding embodiments, wherein the hydrogenation unit comprises a first catalyst within a first reactor and a second catalyst within a second reactor.

Embodiment 8

The method of any of the preceding embodiments, further comprising adding hydrogen to the first process stream prior to passing through the selective hydrogenation unit.

Embodiment 9

The method of any of the preceding embodiments, wherein greater than or equal to 90% of any 1-butene present in the second process stream is converted to 2-butene within the hydroisomerization unit.

Embodiment 10

The method of any of the preceding embodiments, wherein the third process stream comprises less than or equal to 0.1% butadiene by weight prior to passing through the hydration unit.

Embodiment 11

The method of any of the preceding embodiments, wherein the third process stream comprises greater than or equal to 0.01 weight %, preferably, 0.25 weight % to 50 weight 1-butene and/or 2-butene prior to passing through the hydration unit.

Embodiment 12

The method of any of the preceding embodiments, wherein the hydration unit comprises an oscillating baffle reactor, a fixed bed reactor, a membrane integrated reactor, or a combination comprising at least one of the foregoing.

Embodiment 13

The method of any of the preceding embodiments, wherein less than 99.9 weight % of any butene present in the third process stream is converted to butanol within the hydration unit, preferably greater than or equal to 75 weight %.

Embodiment 14

The method of any of the preceding embodiments, further comprising withdrawing the fuel additive product from the hydration unit.

Embodiment 15

The method of Embodiment 14, wherein the fuel additive product comprises 2-butanol, tert-butyl alcohol, di-isobutene, dimers of 1-butene, dimers of 2-butene, dimers of isobutene, or a combination comprising at least one of the forgoing.

Embodiment 16

The method of Embodiment 14, wherein the fuel additive product comprises greater than or equal to 1.0 weight % trimethylpentane, preferably 0.1 to 25 weight %, more preferably 1 to 20 weight %.

Embodiment 17

The method of Embodiment 14, wherein an octane number of the fuel additive product is greater than 80, preferably, greater than 82, more preferably, greater than 85, more preferably, greater than 87, even more preferably, greater than 90 according to the Anti-Knock Index.

Embodiment 18

The method of Embodiment 14, wherein a Reid vapor pressure of the fuel additive product is less than or equal to 65 kiloPascals.

Embodiment 19

The method of any of the preceding embodiments, further comprising passing a bottom stream of the isomerization unit through a metathesis unit and withdrawing a propylene product from the metathesis unit.

Embodiment 20

A method of producing a fuel additive, comprising: passing a first feed stream comprising C4 hydrocarbons through a catalytic cracking unit producing a second feed stream, wherein the first feed stream comprises ethyl acetylene, vinyl acetylene, 1,3-butadiene, 1,2-butadiene, isobutylene, cis-2-butene, trans-2-butene, 1-butene, isobutane, n-butane, or a combination comprising at least one of the foregoing; passing the second feed stream through a methyl tertiary butyl ether unit producing a first process stream and a methyl tertiary butyl ether product and withdrawing the methyl tertiary butyl ether product from the methyl tertiary butyl ether unit, wherein less than 99.99% of any isobutylene present in the feed stream is converted to methyl tertiary butyl ether within the methyl tertiary butyl ether unit; passing the first process stream through a hydrogenation unit producing a second process stream, wherein greater than or equal to 90% of any butadiene present in the first process stream is converted to 2-butene, 1-butene and n-butane within the hydrogenation unit; passing the second process stream through an isomerization unit producing a third process stream, wherein less than or equal to 99.99% of any 1-butene present in the second process stream is converted to 2-butene within the isomerization unit; passing the third process stream through a hydration unit, wherein the third process stream comprises less than or equal to 0.1% butadiene by weight prior to passing through the hydration unit; withdrawing a fuel additive product from the hydration unit, wherein the fuel additive product comprises greater than 0.1% trimethylpentane; withdrawing a raffinate stream from the hydration unit and recycling the raffinate stream to the catalytic cracking unit; and passing a bottom stream of the isomerization unit through a metathesis unit and withdrawing a propylene product from the metathesis unit.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of producing a fuel additive, comprising:
    passing a feed stream comprising C4 hydrocarbons through a methyl tertiary butyl ether unit producing a first process stream and a methyl tertiary butyl ether product, the feed stream comprising isobutylene, butadiene, 1-butene and 2-butene;
    passing the first process stream through a selective hydrogenation unit producing a second process stream, the selective hydrogenation unit comprising a first reactor stage, a second reactor stage and a third reactor stage in series, the first and second reactor stages converting at least a portion of butadiene present in the first process stream to 2-butene, and a final hydrogenation reaction is achieved in the third reactor stage to produce the second process stream, the yield from butadiene of the first process stream to 2-butene of the second process stream is greater than or equal to 30% and the yield from butadiene of the first process stream to 1-butene of the second process stream is greater than 65%;
    passing the second process stream through an isomerization unit producing a third process stream, wherein at least a portion of 1-butene present in the second process stream is converted to 2-butene within the isomerization unit, and wherein the third process stream exiting the isomerization unit comprises greater than or equal to 50% by weight 2-butene;
    passing the third process stream through a hydration unit producing the fuel additive and a recycle stream, wherein at least a portion of butene present in the third process stream is converted to butanol within the hydration unit; and
    passing a bottom stream of the isomerization unit through a metathesis unit, and passing an ethylene stream through the metathesis unit, and withdrawing a propylene product from the metathesis unit;

wherein the third process stream comprises less than or equal to 1.0% butadiene by weight prior to passing through the hydration unit;

wherein the selective hydrogenation unit comprises a first catalyst within the first reactor stage and a second catalyst within the second reactor stage; and wherein the first reactor stage is operated at a temperature of from 40 to 70° C. and a pressure of from 140 to 400 psig, and the second reactor stage is operated at a temperature of from 50 to 60° C. and a pressure of from 140 to 400 psig, and the third reactor stage is operated at a temperature of from 60 to 80° C. and a pressure of from 250 to 270 psig.

2. The method of claim 1, wherein a source of the feed stream comprises a product of a catalytic cracking process and/or an olefin production process.

3. The method of claim 1, wherein the feed stream comprises ethyl acetylene, vinyl acetylene, 1,3-butadiene, 1,2-butadiene, isobutylene, cis-2-butene, trans-2-butene, 1-butene, isobutane, n-butane, or a combination comprising at least one of the foregoing.

4. The method of claim 1, wherein greater than or equal to 90% of any isobutylene present in the feed stream is converted to methyl tertiary butyl ether within the methyl tertiary butyl ether unit.

5. The method of claim 1, further comprising withdrawing the methyl tertiary butyl ether product from the methyl tertiary butyl ether unit; and wherein the purity of the methyl tertiary butyl ether product is greater than or equal to 90%.

6. The method of claim 1, wherein the first process stream comprises butadiene, and wherein greater than or equal to 90% of the butadiene present in the first process stream is converted to 1-butene, 2-butene, n-butane, or a combination comprising at least one of the foregoing within the selective hydrogenation unit.

7. The method of claim 1
wherein the butadiene content exiting the first reactor stage is 7% or less, and the butadiene content exiting the second reactor stage is 1% or less, and the butadiene content exiting the third reactor stage is less than 0.01%.

8. The method of claim 1, further comprising adding hydrogen to the first process stream prior to passing through the first reactor stage of the selective hydrogenation unit; and
wherein carbon monoxide is injected into the third reactor stage at a rate of two parts per million or greater of a reactor stage feed stream to the third reactor stage.

9. The method of claim 1, wherein greater than or equal to 90% of any 1-butene present in the second process stream is converted to 2-butene within the isomerization unit.

10. The method of claim 1, wherein the third process stream comprises less than or equal to 0.1% butadiene by weight prior to passing through the hydration unit.

11. The method of claim 1, wherein the fuel additive comprises less than or equal to 0.1% by weight of butylene dimers.

12. The method of claim 1, wherein the hydration unit comprises an oscillating baffle reactor, a fixed bed reactor, a membrane integrated reactor, or a combination comprising at least one of the foregoing.

13. The method of claim 1, wherein greater than or equal to 75 weight % to less than 99.9 weight % of any butene present in the third process stream is converted to butanol within the hydration unit.

14. The method of claim 1, further comprising withdrawing the fuel additive from the hydration unit.

15. The method of claim 14, wherein the fuel additive comprises 2-butanol, tert-butyl alcohol, di-isobutene, dimers of 1-butene, dimers of 2-butene, dimers of isobutene, or a combination comprising at least one of the foregoing.

16. The method of claim 14, wherein the fuel additive comprises 1 to 50 weight % trimethylpentane.

17. The method of claim 14, wherein an octane number of the fuel additive is greater than 80 according to the Anti-Knock Index.

18. The method of claim 14, wherein a Reid vapor pressure of the fuel additive is less than or equal to 65 kiloPascals.

19. The method of claim 1, wherein the withdrawn propylene product has a purity of greater than or equal to 98%.

20. A method of producing a fuel additive, comprising:
passing a first feed stream comprising C4 hydrocarbons through a catalytic cracking unit producing a second feed stream, wherein the first feed stream comprises ethyl acetylene, vinyl acetylene, 1,3-butadiene, 1,2-butadiene, isobutylene, cis-2-butene, trans-2-butene, 1-butene, isobutane, n-butane, or a combination comprising at least one of the foregoing;
passing the second feed stream through a methyl tertiary butyl ether unit producing a first process stream and a methyl tertiary butyl ether product and withdrawing the methyl tertiary butyl ether product from the methyl tertiary butyl ether unit, wherein greater than 90% of any isobutylene present in the feed stream is converted to methyl tertiary butyl ether within the methyl tertiary butyl ether unit;
passing the first process stream through a hydrogenation unit producing a second process stream, wherein greater than or equal to 90% of any butadiene present in the first process stream is converted to 2-butene, 1-butene and n-butane within the hydrogenation unit, the selective hydrogenation unit comprising a first reactor stage, a second reactor stage and a third reactor stage in series, the first and second reactor stages converting at least a portion of butadiene present in the first process stream to 2-butene, and a final hydrogenation reaction is achieved in the third reactor stage to produce the second process stream, the yield from butadiene of the first process stream to 2-butene of the second process stream is greater than or equal to 30% and the yield from butadiene of the first process stream to 1-butene of the second process stream is greater than 65%;
passing the second process stream through an isomerization unit producing a third process stream, wherein greater than or equal to 90% of any 1-butene present in the second process stream is converted to 2-butene within the isomerization unit, and wherein the third process stream exiting the isomerization unit comprises greater than or equal to 50% by weight 2-butene;
passing the third process stream through a hydration unit, wherein the third process stream comprises less than or equal to 0.1% butadiene by weight prior to passing through the hydration unit, and wherein greater than or equal to 75 weight % of butene present in the third process stream is converted to butanol within the hydration unit;
withdrawing a fuel additive product from the hydration unit, wherein the fuel additive product comprises greater than 1.0 weight % trimethylpentane;
withdrawing a raffinate stream from the hydration unit and recycling the raffinate stream to the catalytic cracking unit, the raffinate stream passing through an additional hydrogenation unit prior to introduction to the catalytic cracking unit; and passing a bottom stream of the isomerization unit through a metathesis unit, and passing an ethylene stream through the metathesis unit, and withdrawing a propylene product from the metathesis unit;

wherein carbon monoxide is injected into the third reactor stage at a rate of two parts per million or greater of a reactor stage feed stream to the third reactor stage;

wherein the selective hydrogenation unit comprises a first catalyst within the first reactor stage and a second catalyst within the second reactor stage; and wherein the first reactor stage is operated at a temperature of from 40 to 70° C. and a pressure of from 140 to 400 psig, and the second reactor stage is operated at a temperature of from 50 to 60° C. and a pressure of from 140 to 400 psig, and the third reactor stage is operated at a temperature of from 60 to 80° C. and a pressure of from 250 to 270 psig.

* * * * *